(12) United States Patent
Wu et al.

(10) Patent No.: US 10,030,018 B2
(45) Date of Patent: Jul. 24, 2018

(54) HYDROXYETHYL SULFONATE OF CYCLIN-DEPENDENT PROTEIN KINASE INHIBITOR, CRYSTALLINE FORM THEREOF AND PREPARATION METHOD THEREFOR

(71) Applicant: Jiangsu Hengrui Medicine Co., Ltd., Lianyungang, Jiangsu (CN)

(72) Inventors: Guaili Wu, Jiangsu (CN); Xiaohui Gao, Jiangsu (CN); Junlei Jia, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/546,405

(22) PCT Filed: Jan. 12, 2016

(86) PCT No.: PCT/CN2016/070636
§ 371 (c)(1),
(2) Date: Jul. 26, 2017

(87) PCT Pub. No.: WO2016/124067
PCT Pub. Date: Aug. 11, 2016

(65) Prior Publication Data
US 2018/0009804 A1    Jan. 11, 2018

(30) Foreign Application Priority Data
Feb. 3, 2015   (CN) .......................... 2015 1 0056995

(51) Int. Cl.
*C07D 471/04*     (2006.01)
*C07C 309/04*     (2006.01)
*A61K 31/519*     (2006.01)

(52) U.S. Cl.
CPC .......... *C07D 471/04* (2013.01); *A61K 31/519* (2013.01); *C07C 309/04* (2013.01); *C07B 2200/13* (2013.01)

(58) Field of Classification Search
CPC .............................. C07D 471/04; A61K 31/519
USPC ..................................... 544/279; 514/264.11
See application file for complete search history.

(56) References Cited

FOREIGN PATENT DOCUMENTS

| CN | 1835951 A | 9/2006 |
|---|---|---|
| CN | 101511829 A | 8/2009 |
| WO | 2014183520 A1 | 11/2014 |

OTHER PUBLICATIONS

Schulz, Molecular Biology of Human Cancers: Chapter 1, Springer, pp. 1-23 (2007).*
Simone, Oncology: Introduction, Cecil Textbook of Medicine, 20th Edition, vol. 1, pp. 1004-101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
O'Leary et al., Treating cancer with selective CDK4/6 inhibitors, Nature Reviews: Clinical Oncology, vol. 13, pp. 417-430 (2016).*
Int'l Search Report dated Apr. 18, 2016 in Int'l Application No. PCT/CN2016/070636.

* cited by examiner

*Primary Examiner* — Deepak R Rao
(74) *Attorney, Agent, or Firm* — Panitch Schwarze Belisario & Nadel LLP (57) ABSTRACT

Provided are a hydroxyethyl sulfonate of a cyclin-dependent protein kinase inhibitor, a crystalline form thereof and a preparation method therefor. Specifically, 6-acetyl-8-cyclopentyl-5-methyl-2-((5-(piperidin-4-yl)pyridin-2-yl)amino)pyrido[2,3-d]pyrimidin-7(8H)-one hydroxyethyl sulfonate (compound of formula (I)), a crystal form I thereof and a preparation method therefor are provided. Crystal form I of the compound of formula (I) has good chemical and crystalline stability, low toxicity, and low residual crystallization solvent. Therefore, the crystal form I can be used in improved clinical therapy.

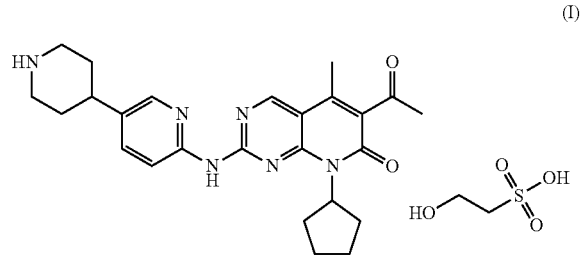

(I)

15 Claims, 2 Drawing Sheets

HYDROXYETHYL SULFONATE OF CYCLIN-DEPENDENT PROTEIN KINASE INHIBITOR, CRYSTALLINE FORM THEREOF AND PREPARATION METHOD THEREFOR

CROSS-REFERENCE TO RELATED APPLICATION

This application is a Section 371 of International Application No. PCT/CN2016/070636, filed Jan. 12, 2016, which was published in the Chinese language on Aug. 11, 2016, under International Publication No. WO 2016/124067 A1, and the disclosure of which is incorporated herein by reference.

FIELD OF THE INVENTION

The present invention relates to a hydroxyethyl sulfonate of a cyclin-dependent kinase (CDK4&6) inhibitor, crystal form I and preparation method thereof.

BACKGROUND OF THE INVENTION

Breast cancer is one of the most common malignant tumors in women, with a high incidence rate and invasiveness, but the course of progression is slow. "Chinese Breast Disease Investigation Report" issued in Beijing on 1 Feb. 2010 by Chinese Population Association showed that the death rate of breast cancer in Chinese urban areas has increased by 38.91%, and that breast cancer has become the greatest threat to women's health. At present, there are at least 156 drugs for breast cancer under development or on the market, in which 68% are targeted drugs. A number of researchers have shown that tumor is related to cell cycle abnormalities, mutations of mitotic signaling proteins and defects of anti-mitotic signaling proteins in tumor cells leading to proliferation disorders. Meanwhile, most of the tumors have genomic instability (GIN) and chromosome complement instability (CIN), and these three basic cell cycle defects are all induced directly or indirectly by out of control of cyclin dependent kinases (CDKs). Cyclin Dependent Kinase (CDK) has become an increasingly popular target.

Currently, many first- and second-generation CDK inhibitors have been developed. The most noticed second-generation drug includes a CDK4&6 inhibitor PD-0332991, which was jointly developed by Pfizer and Onyx. It inhibits the phosphorylation of Rb by inhibiting the activity of CDK4&6, enables the E2F-Rb complex to be detained in the cytoplasm, and blocks initiation of the cell cycle. The results of a clinical trial (NCT00721409) showed that the progression-free survival (PFS) of patients treated with letrozole alone was 7.5 months, whereas the progression-free survival of patients subjected to combined treatment of letrozole and PD-0332991 was extended to 26.1 months. This remarkable advantage has received widespread attention. At the beginning of 2013, the FDA considered that it might be a groundbreaking anticancer drug after reviewing the mid-term result of the drug.

International Patent Application Publication WO2014183520 discloses CDK4&6 inhibitors similar to PD-0332991 in structure, with significant inhibitory activity and high selectivity for CDK4&6, comprising the following compound:

However, this compound has poor solubility, and cannot be used directly as a drug. There is a need to find a pharmaceutically acceptable form, which makes it possible to enhance its solubility and bioavailability.

On the other hand, it is known to those skilled in the art that the crystal structure of the pharmaceutically active ingredient often affects the chemical stability of the drug. Different crystallization conditions and storage conditions can lead to changes in the crystal structure of the compound, and sometimes the accompanying production of other crystal forms. In general, an amorphous drug product does not have a regular crystal structure, and often has other defects such as poor product stability, smaller particle size, difficult filtration, easy agglomeration, and poor liquidity. Thus, it is necessary to improve the various properties of the above product. There is a need to identify a new crystal form with high purity and good chemical stability.

SUMMARY OF THE INVENTION

The present invention provides a 6-acetyl-8-cyclopentyl-5-methyl-2-((5-(piperidin-4-yl)pyridin-2-yl)amino)pyrido[2,3-d]pyrimidin-7(8H)-one hydroxyethyl sulfonate (as shown in formula (I)).

The compound of formula (I) can be obtained by reacting tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate with hydroxyethyl sulfonic acid.

The solubility of the compound of formula (I) has been greatly improved compared to 6-acetyl-8-cyclopentyl-5-methyl-2-((5-(piperidin-4-yl)pyridin-2-yl)amino)pyrido[2,3-d]pyrimidin-7(8H)-one. Its solubility in water reaches 8.33 mg/mL.

In another aspect, the present invention provides crystal form I of the compound of formula (I).

Figure 1:
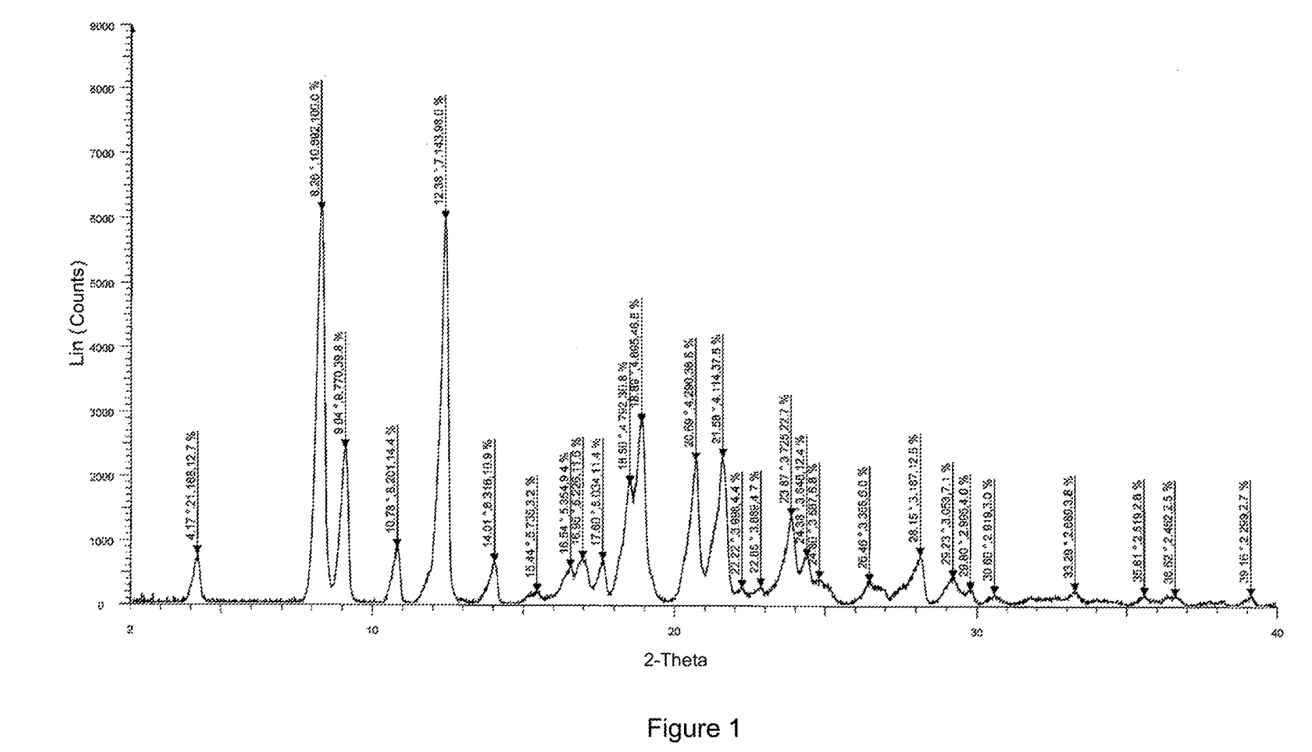
FIG. 1 shows the X-ray powder diffraction spectrum of crystal form I of the compound of formula (I)

A series of crystal products of the compound of formula (I) have been obtained under various crystallization conditions, and X-ray diffraction and differential scanning calorimetry (DSC) measurement have been conducted on the crystal products obtained. It was found that a stable crystal form of the compound of formula (I), which is referred to as crystal form I, can be obtained under normal crystallization conditions. The DSC spectrum of crystal form I of the present application shows a melting endothermic peak at about 324° C. The X-ray powder diffraction spectrum, which is obtained by using Cu-Ka radiation and represented by 2θ angle and interplanar spacing (d value), is shown in FIG. 1, in which there are characteristic peaks at 4.17 (21.17), 8.26 (10.69), 9.04 (9.77), 10.78 (8.20), 12.38 (7.14), 14.01 (6.32), 18.50 (4.79), 18.89 (4.70), 20.69 (4.29), 21.58 (4.11), 23.87 (3.73) and 28.15 (3.17).

The present invention also provides a method for preparing crystal form I of 6-acetyl-8-cyclopentyl-5-methyl-2-((5-(piperidin-4-yl)pyridin-2-yl)amino)pyrido[2,3-d]pyrimidin-7(8H)-one hydroxyethyl sulfonate. The method comprises the following steps of:

1) dissolving tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate and hydroxyethyl sulfonic acid, or any crystal form or amorphous form of the compound of formula (I) into a crystallization solvent to precipitate a crystal; or to precipitate a crystal after adding an anti-solvent, wherein the crystallization solvent is selected from water, an organic solvent, or a mixed solvent of water and an organic solvent; the organic solvent is at least one selected from alcohols, ketones and nitriles having 3 or less carbon atoms, or a mixed solvent of at least one solvent mentioned above and a halohydrocarbon having 3 or less carbon atoms; the anti-solvent is at least one selected from alcohols, ketones and nitriles having 3 or less carbon atoms; and 2) filtering the crystal, then washing and drying it.

In a preferable embodiment of the present invention, the crystallization solvent of step 1) is methanol/water, ethanol/water, isopropanol/water, acetone/water or acetonitrile/water, wherein most preferably the organic solvent is ethanol/water, and the ratio of the two is not particularly limited. In a preferred embodiment of the present invention, the volume ratio of the two is 3:1. In a preferred embodiment of the present invention, the anti-solvent of step 1) is methanol, ethanol, isopropanol, acetone or acetonitrile, wherein most preferably the anti-solvent is ethanol.

The present invention also provides a compound, i.e., tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate. This compound is useful in the preparation of the desired compound of formula (I) and crystal form I thereof of the present invention.

The crystallization method is not particularly limited, and can be carried out by a conventional crystallization process. For example, the material, i.e., the compound of formula (I), can be dissolved in an organic solvent under heating, then an anti-solvent is added to precipitate a crystal by cooling. After the completion of crystallization, the desired crystal can be obtained via filtering and drying. In particular, the crystal obtained by filtration is usually dried in a vacuum under reduced pressure at a heating temperature of about 30 to 100° C., preferably 40 to 60° C., to remove the crystallization solvent.

The resulting crystal form of the compound of formula (I) is determined by differential scanning calorimetry (DSC) and X-ray diffraction spectra. Meanwhile, the residual solvent in the obtained crystal is also determined.

Crystal form I of the compound of formula (I) prepared according to the method of the present invention does not contain or contains only a relatively low content of residual solvent, which meets the requirement of the National Pharmacopoeia concerning the limitation of the residual solvent of drug products. Therefore, the crystal of the present invention is suitable for use as a pharmaceutical active ingredient.

The research results show that crystal form I of the compound of formula (I) prepared according to the present invention is stable under conditions of lighting, high temperature and high humidity. Crystal form I is also stable under conditions of grinding, pressure and heating, which meets the production, transportation and storage requirements of drug products. The preparation process thereof is stable, reproducible and controllable, which is suitable for industrial production.

DETAILED DESCRIPTION OF THE INVENTION

The present invention is illustrated by the following examples in detail. The examples of the present invention are merely intended to describe the technical solution of the present invention, and should not be considered as limiting the scope of the present invention.

Test Instruments Used in the Experiments
1. DSC Spectrum
Instrument type: Mettler Toledo DSC 1 Staree System
Purging gas: Nitrogen
Heating rate: 10.0° C./min
Temperature range: 40-300° C.
2. X-Ray Diffraction Spectrum
Instrument type: Bruker D8 Focus X-ray powder diffractometer
Ray: monochromatic Cu-Kα ray (λ=1.5406)
Scanning mode: θ/2θ, Scanning range: 2-40°
Voltage: 40 KV, Electric current: 40 mA

Example 1

Preparation of 6-acetyl-8-cyclopentyl-5-methyl-2-((5-(piperidin-4-yl)pyridin-2-yl)amino)pyrido[2,3-d]pyrimidin-7(8H)-one hydroxyethyl sulfonate Step 1: Preparation of tert-butyl 6-((6-(1-butoxyethenyl)-8-cyclopentyl-5-methyl-7-oxo-7,8-dihydropyrido[2,3-d]pyrimidin-2-yl)amino)-5',6'-dihydro-[3,4'-bipyridyl]-1'(2'H)-formate Step 1

2-Amino-6-(1-butoxyethenyl)-8-cyclopentyl-5-methyl-pyrido[2,3-d]pyrimidin-7(8H)-one (prepared according to the method disclosed in International Patent Application Publication WO2014183520) (10 g, 29.06 mmol), cesium carbonate (14.22 g, 43.75 mmol), Pd$_2$(dba)$_3$ (2.12 g, 2.31 mmol), 4,5-bis(diphenylphosphine)-9,9-dimethyl xanthene (2.69 g, 4.69 mmol) and 125.00 g of dioxane were added to a three-necked reaction flask under argon, and the mixture was stirred well and heated to reflux. A mixed solution of the material tert-butyl 4-(6-chloropyridin-3-yl)-5,6-dihydro-pyridin-1(2H)-carboxylate (10.34 g, 35.00 mmol, purchased from Yancheng Ruikang Pharmaceutical Chemical Co., Ltd.) and dioxane (65.62 g, 0.74 mol) was slowly added dropwise for about 5 hours. After completion of dropwise addition, the reaction mixture was refluxed for another 1-1.5 hours under stirring. The reaction process was monitored by TLC until the starting material 2-amino-6-(1-butoxyethe-nyl)-8-cyclopentyl-5-methylpyrido[2,3-d]pyrimidin-7(8H)-one was used completely (eluent: petroleum ether:ethyl acetate=2:1, $R_f$ of starting material=0.6, $R_f$ of product=0.7), then the reaction was terminated. The reaction solution was cooled to room temperature and filtered, and the filter cake was washed with dichloromethane (17.19 g×3). The filtrate was concentrated to dryness under reduced pressure at 65° C. Then, dichloromethane (137.50 g) was added to dissolve the residue, then 56.25 g of purified water were added. The reaction solution was separated, and the aqueous phase was extracted with 68.75 g of dichloromethane. The organic phases were combined, dried over anhydrous sodium sulfate, and filtered The filter cake was washed with 23.44 g of dichloromethane, and the filtrate was concentrated to obtain an oily liquid under reduced pressure at 45° C. Acetone (150 g) was added, then the mixture was stirred for about 2 hours at room temperature, and stirred for about 3 hours in an ice water bath. The mixture was filtered, the filter cake was washed with cold acetone (25 g×4), and dried at room temperature under reduced pressure for 8-10 hours to obtain a solid (about 14.84 g), in a yield of 80-92%, with a purity detected by HPLC of not less than 90%. ESI/MS:[M+H]=601.43.

Step 2: Preparation of tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate

Tert-butyl 6-((6-(1-butoxyethenyl)-8-cyclopentyl-5-methyl-7-oxo-7,8-dihydropyrido[2,3-d]pyrimidin-2-yl)amino)-5',6'-dihydro-[3,4'-bipyridyl]-1'(2'H)-formate (14.84 g, 24.69 mmol) and 75 g of acetic acid were added to a three-necked reaction flask under argon. 10% Pd/C (5 g) was added, the flask was purged with hydrogen three times, and the hydrogenation reaction was carried out at 50-60° C. under stirring and normal pressure for 30-32 hours. When the remaining amount of the intermediate state (an intermediate derived from tert-butyl 6-((6-(1-butoxyethenyl)-8-cyclopentyl-5-methyl-7-oxo-7,8-dihydropyrido[2,3-d]pyrimidin-2-yl)amino)-5',6'-dihydro-[3,4'-bipyridyl]-1'(2'H)-formate, wherein the protecting group of tert-butyl has been removed while the double bond has not yet been reduced) is <0.3% monitored by HPLC, the reaction was terminated. The reaction solution was cooled to room temperature, and the system was purged with argon. Then, the reaction solution was filtered, and the filter cake was washed with 37.50 g of dichloromethane. The filtrate was concentrated to dryness at 65° C. under reduced pressure. The residue was dissolved in 50 g of anhydrous ethanol and heated to reflux for 0.5 hours under argon, then the mixture was naturally cooled to room temperature under stirring, and stirred in an ice bath for about 4 hours. The mixture was filtered, and the filter cake was washed with cold anhydrous ethanol (12.50 g×2). The wet product obtained was stirred in 31.25 g of dichloromethane, and the insoluble material was filtered. Isopropanol (118.75 g) was slowly added to the filtrate under stirring. The mixture was stirred for about 3 hours in an ice bath, filtered and dried under reduced pressure for 8-10 hours to obtain a solid (about 8.75 g) in a yield of 60-72%, with a purity detected by HPLC of not less than 98%. ESI/MS:[M+H]=547.26.

Figure 2:
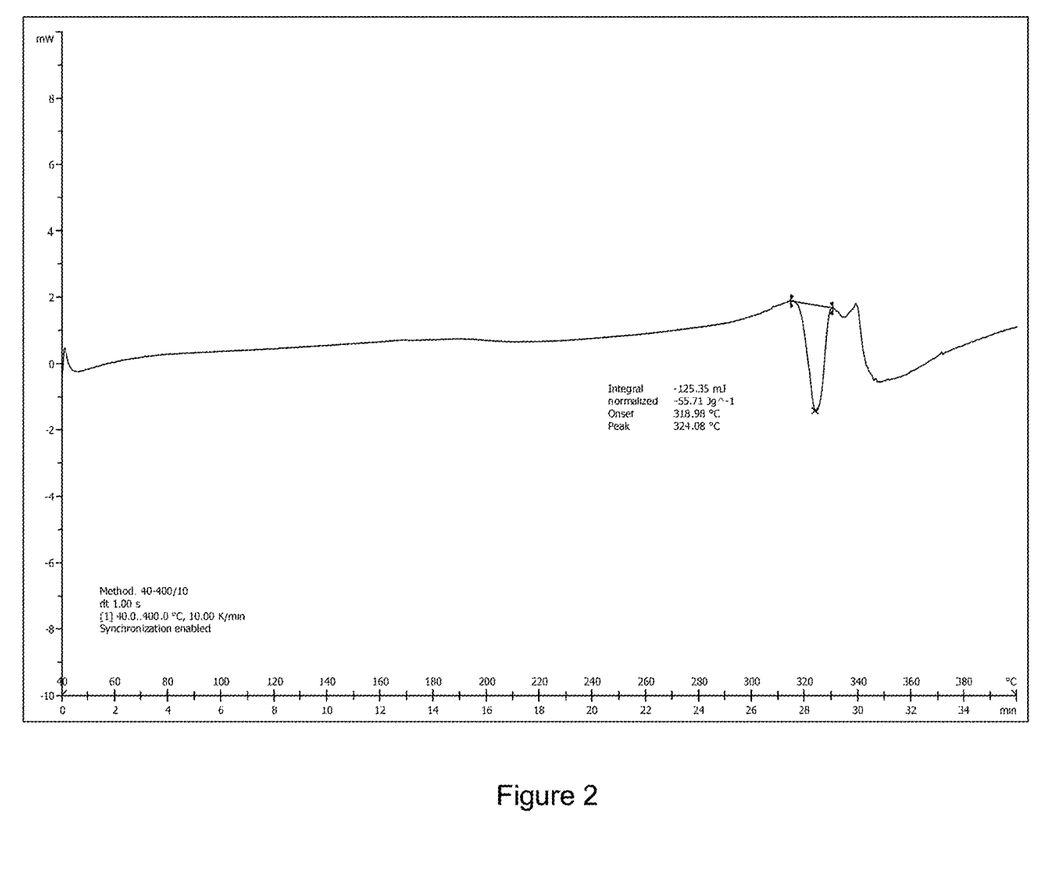
FIG. 2 shows the DSC spectrum of crystal form I of the compound of formula (I).

Step 3: Preparation of 6-acetyl-8-cyclopentyl-5-methyl-2-((5-(piperidin-4-yl)pyridin-2-yl)amino)pyrido[2,3-d]pyrimidin-7(8H)-one hydroxyethyl sulfonate Tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate (8.75 g, 15.94 mmol) and 56.25 g of anhydrous methanol were added to a three-necked reaction flask, and stirred well. Then, 80% hydroxyethyl sulfonic acid (8.81 g, 55.94 mmol) and 0.94 g of water were dissolved in 13.75 g of anhydrous methanol, and added dropwise to the above solution, which then became clear. After completion of dropwise addition, the reaction mixture was refluxed for 3-3.5 hours under stirring. The reaction process was monitored by TLC until the starting material was used completely (petroleum ether:ethyl acetate=1:1, $R_f$ of starting material=0.3, $R_f$ of product=0), then the reaction was terminated and filtered while it was hot. Triethylamine (4.00 g, 39.38 mmol) was added dropwise to the filtrate under stirring. After completion of dropwise addition, the mixture was stirred for about 1 hour, and stirred in an ice bath for about 3 hours. The mixture was filtered, the filter cake was washed with cold anhydrous methanol (7.19 g×2), dried at 40° C. under reduced pressure for 6-8 hours to obtain a solid (about 7.97 g) in a yield of 82-93%, with a purity detected by HPLC of not less than 98%. TOF-MS: [M+H]=447.2503 (an ion peak of 6-acetyl-8-cyclopentyl-5-methyl-2-((5-(piperidin-4-yl)pyridin-2-yl)amino)pyrido[2,3-d]pyrimidin-7(8H)-one binding with one hydrogen ion). The X-ray powder diffraction spectrum of the crystal sample is shown in FIG. 1, in which there are characteristic peaks at 4.17 (21.17), 8.26 (10.69), 9.04 (9.77), 10.78 (8.20), 12.38 (7.14), 14.01 (6.32), 18.50 (4.79), 18.89 (4.70), 20.69 (4.29), 21.58 (4.11), 23.87 (3.73) and 28.15 (3.17). The DSC spectrum is shown in FIG. 2, having a melting endothermic peak at about 324° C. The crystal form was defined as crystal form I.

Example 2

The compound of formula I (1.0 g, 1.75 mmol) was added to a 50 ml one-necked flask, followed by addition of 11 mL of 75% ethanol. The mixture was heated to reflux under stirring until the solution was clear. The mixture was filtered while it was hot, and anhydrous ethanol (11 mL) was slowly added to the filtrate under stirring. The mixture was naturally cooled to room temperature to precipitate a crystal under stirring. The mixture was filtered, washed and dried to obtain a solid (860 mg, yield: 82.1%). The product was identified as crystal form I after studying and comparing the X-ray diffraction and DSC spectra.

Example 3

The compound of formula I (1.0 g, 1.75 mmol) was added to a 25 ml one-necked flask, followed by addition of 2.5 mL of water. The mixture was heated to reflux until the solution was clear, then 15 mL of ethanol was added slowly. The mixture was cooled to precipitate a crystal under stirring. On the next day, the mixture was filtered and dried to obtain a white solid (268 mg, yield: 53.6%). The product was identified as crystal form I after studying and comparing the X-ray diffraction and DSC spectra.

Example 4

The compound of formula I (1.0 g, 1.75 mmol) was added to a 25 ml one-necked flask, followed by addition of 2.5 mL of water. The mixture was heated to reflux until the solution was clear, then isopropanol (15 mL) was added slowly. The mixture was cooled to precipitate a crystal under stirring. On the next day, the mixture was filtered and dried to obtain a white solid (201 mg, yield: 40.2%). The product was identified as crystal form I after studying and comparing the X-ray diffraction and DSC spectra.

Example 5

The compound of formula I (1.0 g, 1.75 mmol) was added to a 25 ml one-necked flask, followed by addition of 2.5 mL of water. The mixture was heated to reflux until the solution was clear, then acetone (15 mL) was added slowly. The mixture was cooled to precipitate a crystal under stirring. On the next day, the mixture was filtered and dried to obtain a white solid (332 mg, yield: 66.4%). The product was identified as crystal form I after studying and comparing the X-ray diffraction and DSC spectra.

Example 6

The compound of formula I (1.0 g, 1.75 mmol) was added to a 25 mL one-necked flask, followed by addition of 2.5 mL of water. The mixture was heated to reflux until the solution was clear, then acetonitrile (15 mL) was added slowly. The mixture was cooled to precipitate a crystal under stirring. On the next day, the mixture was filtered and dried to obtain a white solid (298 mg, yield: 59.6%). The product was identified as crystal form I after studying and comparing the X-ray diffraction and DSC spectra.

Example 7

The compound of formula I (1.0 g, 1.75 mmol) was added to a 25 mL one-necked flask, followed by addition of 4 mL of 75% ethanol. The mixture was heated to reflux until the solution was clear, then ethanol (4 mL) was added slowly. The mixture was cooled to precipitate a crystal under stirring. On the next day, the mixture was filtered and dried to obtain a white solid (407 mg, yield: 81.4%). The product was identified as crystal form I after studying and comparing the X-ray diffraction and DSC spectra.

Example 8

The compound of formula I (1.0 g, 1.75 mmol) was added to a 25 ml one-necked flask, followed by addition of 4 mL of 75% ethanol. The mixture was heated to reflux until the solution was clear, then ethanol (4 mL) was added slowly. The mixture was cooled to precipitate a crystal under stirring. On the next day, the mixture was filtered and dried to obtain a white solid (418 mg, yield: 83.6%). The product was identified as crystal form I after studying and comparing the X-ray diffraction and DSC spectra.

Example 9

The product sample of crystal form I prepared in Example 1 was spread flat in the air to test its stability under conditions of lighting (4500 Lux), heating (40° C., 60° C.), and high humidity (RH 75%, RH 90%). Samplings were carried out on Day 5 and Day 10. The purity as detected by HPLC is shown in Table 1.

TABLE 1

| Stability comparison of crystal form I of the compound of formula (I) | | | | | | |
|---|---|---|---|---|---|---|
| Batch number | Time (day) | Light-ing | 40° C. | 60° C. | RH 75% | RH 90% |
| S011305130806 | 0 | 99.36% | 99.36% | 99.36% | 99.36% | 99.36% |
|  | 5 | 99.36% | 99.40% | 99.40% | 99.33% | 99.36% |
|  | 10 | 99.38% | 99.40% | 99.38% | 99.34% | 99.37% |

The results of the stability study showed that crystal form I of the compound of formula (I) had good stability when it was spread flat in the air under conditions of lighting, high temperature and high humidity.

Example 10

Crystal form I of the compound of formula (I) prepared according to the method of Example 1 was ground, heated and pressed. The results showed that the crystal form is stable. The detailed experimental data are shown in Table 2 below.

TABLE 2

| Special stability study of crystal form I of the compound of formula (I) | | | | |
|---|---|---|---|---|
| Batch number | Treatment Process | Experimental procedure | Crystal form | DSC peak |
| S011305130808G | Grinding treatment for 10 min | 1 g sample of crystal form I of the compound of formula (I) was ground for 10 min in a mortar under nitrogen atmosphere. | Crystal form I | DSC peak 324.71° C. |

TABLE 2-continued

Special stability study of crystal form I of the compound of formula (I)

| Batch number | Treatment Process | Experimental procedure | Crystal form | DSC peak |
|---|---|---|---|---|
| S011305130808H | Heating treatment for 3 h at 80° C. | 1 g sample of crystal form I of the compound of formula (I) was spread flat and heated at 80° C. for 3 h. | Crystal form I | DSC peak 324.77° C. |
| S011305130808P | Pressing treatment | Sample of crystal form I of the compound of formula (I) was pressed to a slice. | Crystal form I | DSC peak 324.42° C. |

What is claimed is:

1. Crystal form I of a compound of formula (I):

(I)

wherein the crystal has a characteristic X-ray powder diffraction spectrum comprising diffraction peaks at diffraction angles (2θ) of about 4.17, 8.26, 9.04, 10.78, 12.38, 14.01, 18.50, 18.89, 20.69, 21.58, 23.87 and 28.15.

2. A method of preparing the crystal form I of the compound of formula (I) according to claim 1, comprising steps of:
   (a) dissolving tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate and hydroxyethyl sulfonic acid, or any crystal form or amorphous form of the compound of formula (I) into a crystallization solvent to precipitate a crystal, wherein the crystallization solvent is selected from the group consisting of water, an organic solvent, and mixtures thereof; the organic solvent is selected from the group consisting of alcohols, ketones, nitriles each of which having 3 or less carbon atoms, and mixtures thereof or alternatively the organic solvent is a mixed solvent of a halogenated hydrocarbon having 3 or less carbon atoms and at least one solvent selected from the group consisting of alcohols, ketones, and nitriles each of which having 3 or less carbon atoms; and
   (b) filtering the crystal, then washing and drying the filtered crystal.

3. A method of preparing the crystal form I of the compound of formula (I) according to claim 1, comprising steps of:
   (a) dissolving tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate and hydroxyethyl sulfonic acid, or any crystal form or amorphous form of the compound of formula (I) into a crystallization solvent, wherein the crystallization solvent is selected from the group consisting of water, an organic solvent, and mixtures thereof, then adding an anti-solvent to precipitate a crystal, wherein the anti-solvent is selected from the group consisting of alcohols, ketones, nitriles each of which having 3 or less carbon atoms, and mixtures thereof; and
   (b) filtering the crystal, then washing and drying it.

4. The method according to claim 2, wherein the crystallization solvent is a mixed solvent of ethanol/water.

5. The method according to claim 3, wherein the crystallization solvent is a mixed solvent of ethanol/water, and the anti-solvent is ethanol.

6. Tert-butyl 4-(6-((6-acetyl-8-cyclopentyl-5-methyl-7-oxo-7,8-dihydropyrido[2,3-d]pyrimidin-2-yl)amino)pyridin-3-yl)piperidine-1-formate.

7. The crystal form (I) of the compound of formula (I) according to claim 1, wherein the crystal has the following interplanar spacing (Å) at each of the indicated diffraction angles (2θ):

| 2θ (°) | Interplanar spacing (Å) |
|---|---|
| 4.17 | 21.17 |
| 8.26 | 10.69 |
| 9.04 | 9.77 |
| 10.78 | 8.20 |
| 12.38 | 7.14 |
| 14.01 | 6.32 |
| 18.50 | 4.79 |
| 18.89 | 4.70 |
| 20.69 | 4.29 |
| 21.58 | 4.11 |
| 23.87 | 3.73 |
| 28.15 | 3.17. |

8. The crystal form I of the compound of formula (I) according to claim 1, wherein a melting point of the crystal is about 324° C.

9. The crystal form I of the compound of formula (I) according to claim 1, wherein the crystal has an X-ray powder diffraction spectrum as shown in FIG. 1.

10. A pharmaceutical composition comprising the crystal form I of the compound of formula (I) according to claim 1 and a pharmaceutically acceptable carrier.

11. A pharmaceutical composition comprising the crystal form I of the compound of formula (I) according to claim 9 and a pharmaceutically acceptable carrier.

12. A method of treating breast cancer in a subject in need thereof, the method comprising administering to the subject the pharmaceutical composition according to claim 10.

13. A method of treating breast cancer in a subject in need thereof, the method comprising administering to the subject the pharmaceutical composition according to claim 11.

14. The method according to claim 12, wherein the crystal has the following interplanar spacing (Å) at each of the indicated diffraction angles (2θ):

| 2θ (°) | Interplanar spacing (Å) |
|---|---|
| 4.17 | 21.17 |
| 8.26 | 10.69 |
| 9.04 | 9.77 |
| 10.78 | 8.20 |
| 12.38 | 7.14 |
| 14.01 | 6.32 |
| 18.50 | 4.79 |
| 18.89 | 4.70 |
| 20.69 | 4.29 |
| 21.58 | 4.11 |
| 23.87 | 3.73 |
| 28.15 | 3.17. |

15. The method according to claim 12, wherein a melting point of the crystal is about 324° C.

* * * * *

Disclaimer

10,030,018 B2 — Guaili Wu, Jiangsu (CN); Xiaohui Gao, Jiangsu (CN); Junlei Jia, Jiangsu (CN). HYDROXYETHYL SULFONATE OF CYCLIN-DEPENDENT PROTEIN KINASE INHIBITOR, CRYSTALLINE FORM THEREOF AND PREPARATION METHOD THEREFOR. Patent dated July 24, 2018. Disclaimer filed March 28, 2019, by the assignee, Jiangsu Hengrui Medicine Co., Ltd.

Hereby disclaims the term of this patent which would extend beyond Patent No. 10,160,759.

*(Official Gazette, November 26, 2019)*